United States Patent
O'Laughlin

Patent Number: 5,295,974
Date of Patent: Mar. 22, 1994

[54] SHIELDED HYPODERMIC NEEDLE WITH I.V. CANNULA

[76] Inventor: D. Michael O'Laughlin, 320 SW. 10th St., #4, Gainesville, Fla. 32601

[21] Appl. No.: 637,674

[22] Filed: Jan. 7, 1991

[51] Int. Cl.⁵ .................................. A61M 5/32
[52] U.S. Cl. .......................... 604/198; 604/171; 604/263
[58] Field of Search .......... 604/263, 198, 192, 162, 604/171, 136

[56] References Cited

U.S. PATENT DOCUMENTS

| | | | |
|---|---|---|---|
| 3,134,380 | 5/1964 | Armao | 604/198 |
| 4,639,249 | 1/1987 | Larson | 604/198 |
| 4,654,030 | 3/1987 | Moll et al. | 604/165 |
| 4,655,751 | 4/1987 | Harbaugh | 604/198 |
| 4,666,435 | 5/1987 | Braginetz | 604/198 |
| 4,675,005 | 6/1987 | DeLuccia | 604/110 |
| 4,702,739 | 10/1987 | Milorad | 604/198 |
| 4,725,267 | 2/1988 | Villancourt | 604/192 |
| 4,747,831 | 5/1988 | Kulli | 604/110 |
| 4,767,413 | 8/1988 | Haber et al. | 604/198 |
| 4,775,367 | 10/1988 | Schmidt | 604/192 |
| 4,795,432 | 1/1989 | Karczmer | 604/110 |
| 4,842,586 | 6/1989 | Hogan | 604/192 |
| 4,846,785 | 7/1989 | Cassou et al. | 604/198 |
| 4,846,805 | 7/1989 | Sitar | 604/165 |
| 4,850,961 | 7/1989 | Wanderer et al. | 604/263 |
| 4,863,434 | 9/1989 | Bayless | 604/198 |
| 4,863,435 | 9/1989 | Sturman et al. | 604/198 |
| 4,863,436 | 9/1989 | Glick | 604/198 |
| 4,887,998 | 12/1989 | Martin et al. | 604/110 |
| 4,892,521 | 1/1990 | Lajco et al. | 604/192 |
| 4,894,055 | 1/1990 | Sudnak | 604/198 |
| 4,900,311 | 2/1990 | Stern et al. | 604/198 |
| 4,906,236 | 3/1990 | Alberts et al. | 604/198 |
| 4,915,697 | 4/1990 | DuPont | 604/192 |
| 4,917,672 | 4/1990 | Terndrup et al. | 604/192 |
| 4,946,446 | 8/1990 | Vadher | 604/263 |
| 4,955,868 | 9/1990 | Klein | 604/263 |
| 4,994,041 | 2/1991 | Dombrowski et al. | 604/198 |
| 5,051,109 | 9/1991 | Simon | 604/263 |

FOREIGN PATENT DOCUMENTS 704152  4/1966  Italy .................... 604/136

Primary Examiner—C. Fred Rosenbaum
Assistant Examiner—Ronald Stright, Jr.
Attorney, Agent, or Firm—David Pressman

[57] ABSTRACT

An I.V. cannula needle (37) has a base adapter (41) with a sleeve (43) which surrounds a compression spring (53) which urges a barrel (47) and its tapered point (49) to cover and protect the point (39) of the I.V. needle (37) An I.V. cannula (52) slips over the barrel (47) and has a winged base (55) which, when pulled backward, compresses a spring (53) inside a base extension (43) and exposes the needle point (39) for insertion. On withdrawing needle (37) and relaxing pull-back pressure, needle point (39) is automatically shielded by the point (49) of the barrel (47), but the loose-fitting I.V. cannula remains in the patient and is taped down and connected to I.V. tubing. A second embodiment comprises a wire (61) which can be manipulated back and forth through a barrel (81) by a winged member (69) operating within a slot (80) and against a spring (67). The wire (61) can protrude through the needle 81 and provide protection against accidental injury from the needle. An I.V. cannula (79) slips over the barrel (81) and is left implanted to receive I.V. tubing.

16 Claims, 3 Drawing Sheets

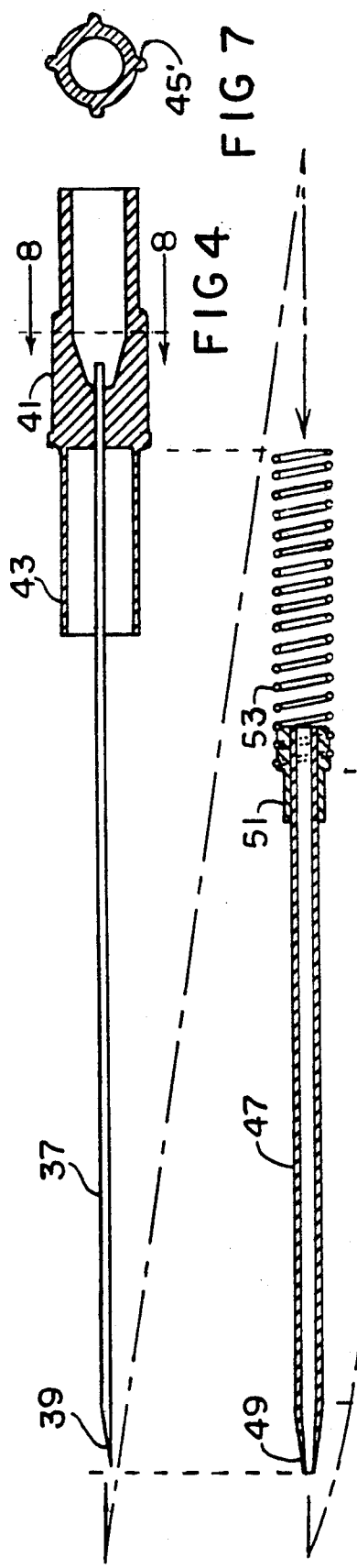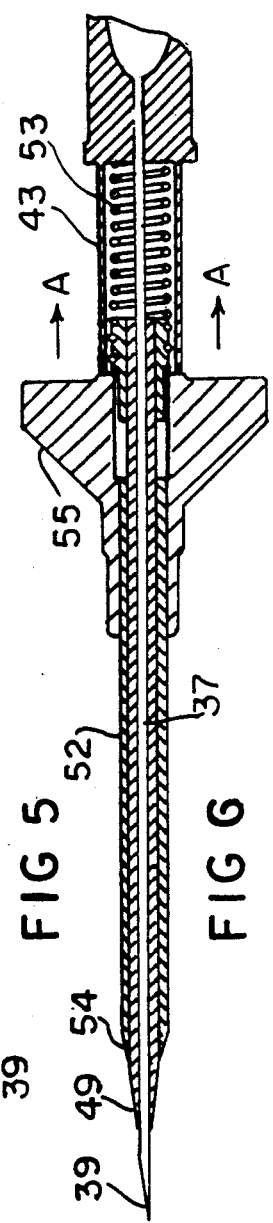

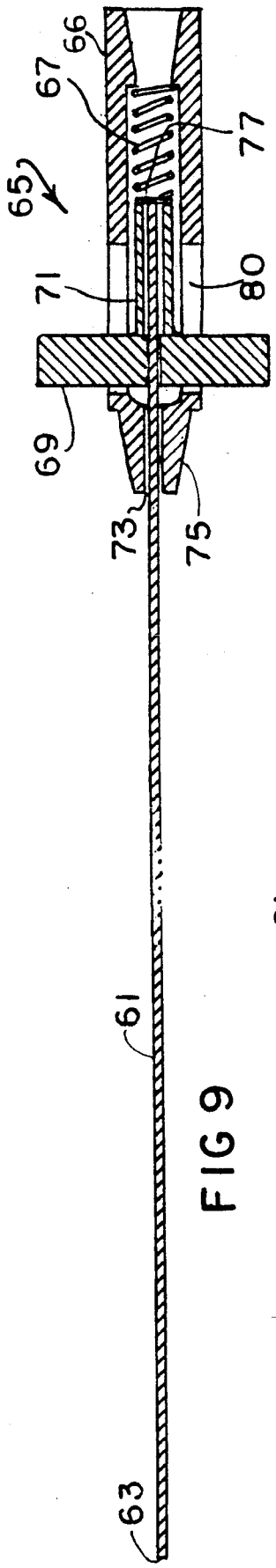
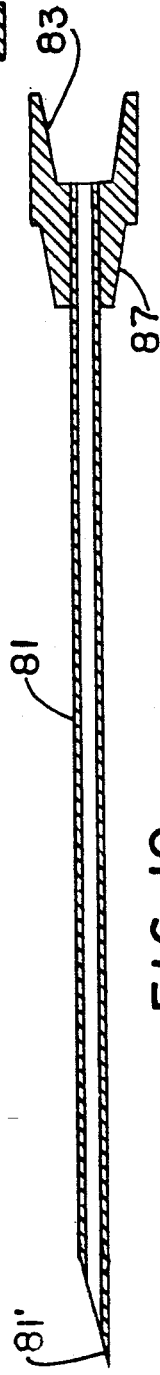
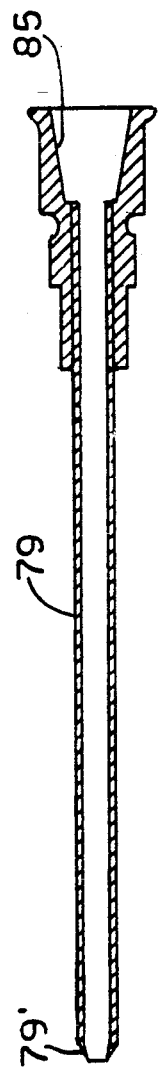
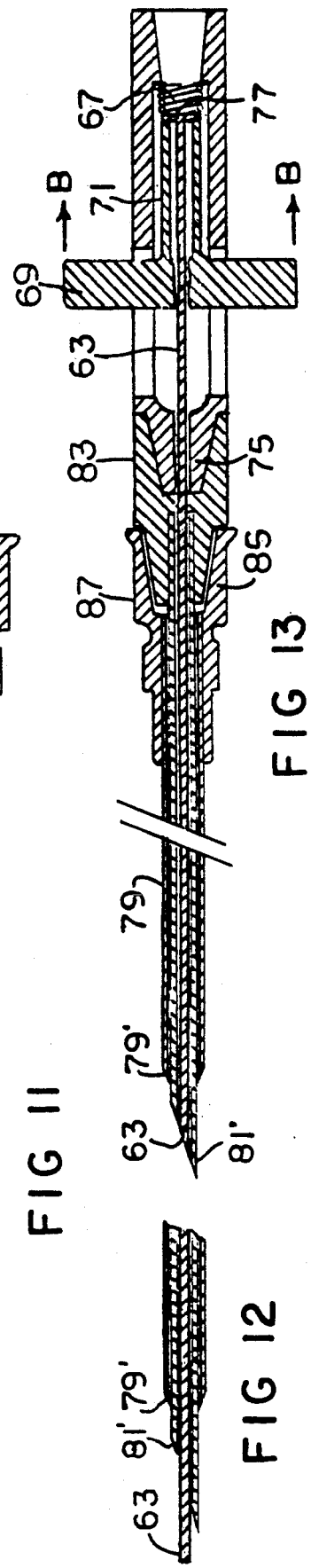
FIG 9
FIG 10
FIG 11
FIG 12
FIG 13

SHIELDED HYPODERMIC NEEDLE WITH I.V. CANNULA

BACKGROUND

1. Field of Invention

The present invention relates to hypodermic needles, in particular to a shielded needle with an I.V. (intravenous) cannula.

2. Field of Prior-Art

In recent years concern has grown amongst hospital staff and health care workers regarding the possibility of getting accidentally stuck with a used hypodermic needle and thereby contracting an infectious disease, such as AIDS. Attempts have been made to design covers, guards, shields and the like for needles, particularly the type used for giving injections.

This form of needle is usually used once. Once the injection has been given, the needle can be placed out of reach of the patient, lessening one area of danger, i.e., the possibility of a mental patient attempting to inflict injury to nurse or doctor with the needle. However, the nurse or doctor can still be accidentally stuck with the needle.

Another problem concerning hypodermic needles occurs when the needle is being used to insert an I.V. cannula. This is because the cannula itself has to remain in the patient and be taped down, but the needle has to be withdrawn and thereby becomes unprotected and potentially dangerus since it can be a source of HIV infection if the user were to be accidentally stuck or pricked. The greatest danger occurs when the nurse or doctor is busy attaching the I.V. tubes to the cannula and securing the tube to the patient with tape; during this time the used and withdrawn hypodermic needle is exposed, unattended and therefore most dangerous. The needle is also exposed and dangerous before insertion.

Heretofore a number of solutions to these problems have been proposed, generally by shielding the hypodermic needle, particularly needles which are used once only for an injectable fluid.

T. Armao, in U.S. Pat. No. 3,134,380, dated May 26, 1964, shows a concertina-type cover which can be manually pulled forward to form a protective cover. Another embodiment in this patent is activated by a spring. However, unless there is sound structural support for the concertina covering, it does not provide a positive protection. Furthermore, no provision is made for use protecting an I.V. cannula inserter.

J. Kulli, in U.S. Pat. No. 4,747,831, dated May 31, 1988, shows a hollow handle which protects a needle and compression spring in the "rest" position. To prepare the needle for use as a cannula inserting needle, it has to be pushed forward so that the needle projects from the end of the handle. At this time the needle is exposed and potentially dangerous. An I.V. cannula can now be fitted over the needle and insertion carried out. A manually operated latch mechanism can now be used to release the needle, whereby the compressed spring carries the needle back into the handle to safety. The problem with this is that once the needle is protruding from the handle and is not shielded, it is dangerous.

V. Vaillancourt, in U.S. Pat. No. 4,725,267, dated Feb. 16, 1988, shows another concertina type cover which incorporates a hard cap which has an aperture at its center. When not in actual use the aperture is not aligned with the needle. However, when it is to be used for either an injection, or positioning an I.V. cannula, the cap's aperture is aligned and pushed down to the base of the syringe, thus exposing the needle. Once again we have an exposed and dangerous needle, especially while an I.V. cannula is being fitted.

J. Laico et al., in U.S. Pat. No. 4,892,521, dated Jan. 9, 1990, shows a cap of hard material covering a syringe needle and supported by guide rods. The cap includes an aperture which can be aligned manually with the needle when it is to be used. This method involves much manipulating around the needle's point with the fingers, which increases the chance of getting accidently stuck, rather than decreasing it.

P. Sudnak, in U.S. Pat. No. 4,894,055, dated Jan. 16, 1990, shows a two-cylinder, spring-activated telescopic arrangment covering the needle. It can be pushed down and locked in that position while the needle is in use, then reactivated after the needle is withdrawn. The problem with this method is that there are times when the needle is completely exposed, and this can happen after the needle has been used. Therefore it is dangerous.

L. Stern, in U.S. Pat. No. 4,900,311, dated Feb. 13, 1990, shows another spring-activated shield. It comprises an elliptical cross-sectioned syringe, having a hypodermic syringe needle attached and a spring-loaded elliptical sheath mounted axially around the syring's body and protruding sufficiently forward to cover the needle. To use, the sheath is pushed back along the shringe body after a cap has been removed from in front of the needle, which also provides an aperture through which the needle can protrude. After use the shield is manually replaced. Again this allows for an exposed needle, and finger manipulation around the needle. Therefore it presents a dangerous device.

F. DuPont, in U.S. Pat. No. 4,915,1990, dated Apr. 10, 1990, shows a needle and its shield within a cover box. When removed from the cover box and fitted onto a syringe, the needle is enclosed in a sheath which has solid end sections with an intermediate callapsible center portion, such that as the needle is injected into the patient the center portion collapses, and when the needle is withdrawn the center portion expands and re-covers the needle. While this may seem to be a well shielded needle, there is nothing to prevent the needle from sticking a nurse or doctor accidentally because the center portion is always able to collapse and allow the needle to penetrate.

T. Terndrup, in U.S. Pat. No. 4,917,672, dated Apr. 17, 1990, shows a shield sleeve covering the point of a hypodermic needle and held in place by a spring whose other end is attached to the syringe. The sleeve can be manipulated by hand to prevent or allow the needle's point to protrude through a hole in the sleeve's end for injection purposes. However, as the needle is being removed from the patient, the spring will automatically reposition the sleeve around and over the point in such a manner that the needle cannot again protrude unless again aligned by hand. No provision is provided for its use in placing an I.V. cannula. Also an I.V. cannula must be inserted at an acute angle to the patient's skin, yet this device must be used in a generally normal manner to the skin.

E. Larson, in U.S. Pat. No. 4,639,249, dated Jan. 27, 1987, shows a latch element which prevents movement of the syringe piston beyond a certain point. No teaching in this reference is directed toward needle protection.

P. Braginetz, in U.S. Pat. No. 4,666,435, dated May 19, 1987, shows an external shield which permits normal usage of the syringe for injection or withdrawing fluids, and which can then be moved into a non-usable locked position. The problem with this unit is that no automation is employed, also, until certain actions are carried out, the exposed needle is a danger.

J. Harbaugh, in U.S. Pat. No. 4,655,741, dated Apr. 7, 1987, shows a slidable cover which can be moved to various positions to cover or uncover the needle as required, This is done manually. No provision is provided to include placing an I.V. cannula in a patient.

C. Karemzer, in U.S. Pat. No. 4,795,432, dated Jan. 3, 1989, shows a flexible needle cover supported by an expanding spring arrangment which can be used to maintain a shield around the needle. However when inserting the needle in a patient, the shield automatically unlocks and allows the needle to be inserted. On withdrawing the needle, the spring automatically repositions the shield around the needle, and prevents subsequent use of the needle. No mention is made as to any possibility of using it for I.V. cannula insertion and the device could not be so used because its size and width will prevent this.

M. Milorad, in U.S. Pat. No. 4,702,739, dated Oct. 27, 1987, shows a slidable cylindrical needle shield, which can be used to both shield the needle and limit the needle's inward penetration, and can be manually extended to reshield the needle when it is withdrawn. The problem is the same as with Karezmer device in that the shield dimension prevents the needle being held almost parallel to the skin which is required to withdraw blood from peripheral veins or when inserting an I.V. cannula needle.

J. DeLuccia, in U.S. Pat. No. 4,675,005, dated Jun. 23, 1987, shows a sleeve enclosing a syringe unit and is locked to its proximal end. In use the syringe is unlocked and pushed forward toward the distal end, thereby exposing the needle and providing it to be used for an injection. Thereafter withdrawal it can be returned to the proximal end for relocking. The problem here again is that its bulk, which is unavoidable due to its construction, makes it unsuitable to be positioned at an acute angle to the patient's skin for insertion of an I.V. cannula needle. No mention is made for this use.

T. Haber, in U.S. Pat. No. 4,767,413, dated Aug. 30, 1988, shows a pull-back shield with self-locking catch pawls, such that the needle can be made to remain extended for administering dental injections, after which the pawls can be released to allow spring action to again extend the shield toward the distal end so as to provide a safe cover for the used needle. The problem here is that manipulation is required to make the used needle safe. No mention is made to use this unit to place an I.V.cannula.

The following patents also disclose various forms of needle protection:

Italian patent 704,152, dated Apr. 1966, R. Davis, U.S. Pat. No. 4,846,804, Mar. 24, 1988; D. Sitar, U.S. Pat. No. 4,846,805, Dec. 4, 1987; M. Glick, U.S. Pat. No. 4,863,436, Oct. 11, 1988; W. Bayless, U.S. Pat. No. 4,863,434, Jan. 9, 1988; M. Sturman, U.S. Pat. No. 4,863,435, filed Aug. 24 1988. However a problem which exists with the needles of all of these references is that automatic protection of the needle immediately after use is not provided.

OBJECTS AND ADVANTAGES

Accordingly several objects and advantages of the invention are to provide a novel hypodermic needle and to provide such a needle which can be used for inserting an I.V. cannula in which the needle is protected before it is inserted, during withdrawal, or after withdrawal. It is always automatically shielded to provide a safer hypodermic needle which is less likely to accidentally prick a medical user, and cannot be used by a mental patient to injure someone purposely. Further objects and advantages will become apparent from a consideration of the ensuing description and accompanying drawings.

BRIEF DESCRIPTION OF DRAWINGS

FIG. 4 is a sectional view of a hypodermic needle of the invention, a sectional view of a barrel of the needle of FIG. 3 with an attached spring, and a sectional view of a cannula according to the invention.

FIG. 5 is a sectional view showing positions of the various points when the needle is at rest.

FIG. 6 is a part sectional view of the needle when it is ready to be used for an injection.

FIG. 7 is an end view of the needle of FIG. 4, taken along the line 8—8 of FIG. 4.

FIG. 8 is an end view of the barrel of FIG. 4.

FIG. 9 is a sectional view of a protecting wire used in an internally or wire protected hypodermic needle according to another embodiment of the invention.

FIG. 10 is a sectional view of an I.V. needle used in the wire-protected embodiment.

FIG. 11 is a sectional view of a cannula used in the wire-protected embodiment.

FIG. 12 is a sectional view of the tip of the wire-protected embodiment when assembled.

FIG. 13 is a sectional view of the wire-protected embodiment ready for injection.

Drawing Reference Numerals

Figure 1:
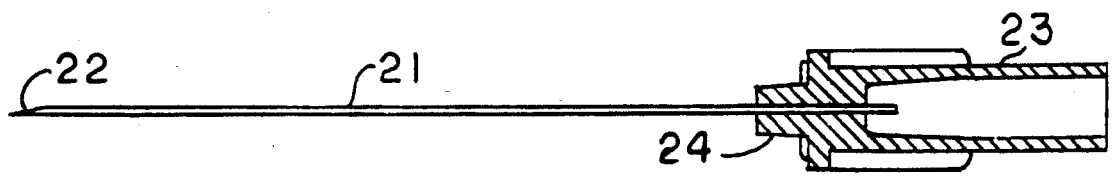
FIG. 1 is a sectional view of a prior-art hypodermic needle.

21 I.V. cannula needle
22 needle point
23 plastic adapter
24 spigot
25 cannula sleeve
27 plastic base
33 narrow end
37 I.V. needle
39 sharp point
41 base adapter
43 tubular extension
45' ridges
47 barrel
49 tapered end
51 base
52 cannula sleeve
53 coil spring
54 tapered end
55 winged base
57 tube adapter
61 wire
63 tip 65 base
66 cylindrical unit
67 spring
69 winged slide
71 plunger
73 guide
75 spigot
77 disc
79 canula
81 canula needle
81' cannula needle point
83 adapter (needle)
83' cannula point'
85 adapter (cannula)
87 spigot

DETAILED DESCRIPTION OF PRIOR-ART HYPODERMIC NEEDLE—FIGS. 1-4

I.V. cannulas are inserted into veins as follows: The cannula is prepackaged with a needle, ready to insert. The I.V. cannula needle is an ordinary hypodermic needle with a specialized base. The nurse or doctor grasps the cannula assembly and inserts the combination so that the cannula follows the needle as it cuts a passageway from the skin to a vein. After having reached the vein, the I.V. needle is withdrawn, leaving the cannula inserted. Then I.V. tubing is attached to the cannula for injecting a medicament or drawing blood.

A prior-art I.V. needle 21 (FIG. 1) is about 50 mm (2") long and about 0.75 mm (0.025") thick, and is attached to a plastic base or adapter 23, which can, in turn, be attached to a syringe (not shown). Needle 21 has a point 22 which is formed by cutting off the end of the needle at an angle.

Figure 2:
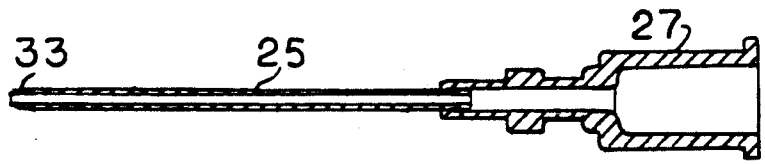
FIG. 2 is a sectional view of a barrel of a prior-art I.V. cannula base and sleeve. hypodermic needlee
Figure 3:
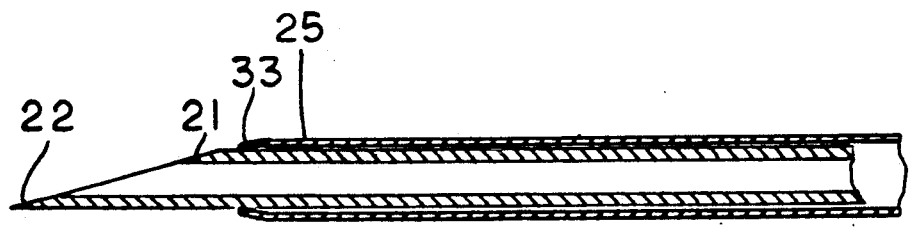
FIG. 3 is a sectional view of the needle of FIGS. 1 and 2 assembled.

A cannula 25 (FIG. 2) is snugly fitted over needle 21 (FIG. 3) and is about 0.32 mm (0.187") long and is tapered at its point 33. It also has a plastic base 27 which fits very loosely over spigot 24 of plastic base adapter 23 of FIG. 1. The lumen of cannula sleeve 25 has a diameter the same as the outer diameter of needle 21. The cannula-needle assembly of FIG. 3 is potentially dangerous as point 22 of needle 21 is exposed.

During penetration of the patient's soft tissue (skin, muscle, and vein wall), needle point 22 leads and cuts a passageway for cannula sleeve 25. The I.V. cannula needle has a diameter of about 0.75 mm and the cannula sleeve about 1.5 mm. Therefore the cannula will fit very tightly in the soft tissue.

Needle 21 and its base adapter 23 are now withdrawn, leaving cannula 25 in position. Needle 21 and its point 22 are now totally unprotected (FIG. 1) and hence potentially dangerous.

EXTERNALLY SHIELDED I.V. NEEDLE—FIGS. 4-8

In accordance with the invention, I provide a safety shield around the needle and its point whenever the needle is not actually penertrating and providing a passageway through the soft tissue. Before the needle is extracted from its fully inserted position, the shield again surrounds the needle's point, so that it is also safely protected when it is withdrawn.

Accordingly, an I.V. needle 37 (FIG. 4) about 70 mm (2.75') long and 0.80 mm (1/32") thick, has a sharp point 39 at its distal end and a plastic base adapter 41 which incorporates a tubular extension cylinder or guideway 43, and has ridges 45' for grasping, as shown in the end view of FIG. 7, taken along the lines 8—8 of FIG. 5.

A 50 mm long barrel 47 is tapered at its distal end 49 and has a base 51 attached to a spring 53 at its proximal end. When barrel 47 is fitted onto needle 37, spring 53 will be housed within extension 43. Spring 53 positions barrel 47 at an appropriate angular position on needle 37 such that tapered end 49 extends distally beyond and thereby covers, surrounds, and protects needle point 39. As in FIGS. 1-3, the lumen of barrel 47 is sized to fit snugly over needle 37.

A cannula sleeve 52, about 35 mm long, has a tapered point 54 at its distal end and a winged base 55 with a tube adapter 57 at its proximal end. This is assembled onto barrel 47. Its lumen fits snugly over barrel 47. When all three parts are assembled and in a "rest" position, their distal ends will appear as shown in FIG. 5. Note that needle point 39 is protected by tapered end 49 of barrel 47 which protrudes from cannula sleeve 52. The proximal end of winged base 55 will be spaced from the distal end of guideway 43 about 8-12 mm.

When needle 37 is to be used, tapered end 49 is first positioned near the patient's skin. Then winged adapter base 55 is pulled backward so as to compress spring 53, as indicated by arrow A in FIG. 6. This slides barrel 47 back along needle 37, thus exposing point 39 for insertion, as is clearly shown in FIG. 6. The proximal end of winged base 55 will be pulled against the distal end of guideway 43.

The nurse now inserts the assembly into the patient in the desired manner. Point 39 of needle 37 leads and cuts a hole through the tissue. Then tapered end 49 of barrel 47 enlarges the hole, followed by cannula 52. Then the nurse withdraws needle 37 and its base and barrel 47 and its base, leaving cannula 52 in position. As soon as the needle and barrel are withdrawn, spring 53 will expand and Immediately reposition end 49 of barrel 47 over needle point 39, thus automatically protecting and shielding point 39 against accidental or purposeful sticking of the user or another person. (The I.V. tube (not shown) can now be inserted into the cannula in the usual manner.)

Note, that point 39 of needle 37 is always shielded, before, during and after insertion.

Internally Protected I.V. Needle—FIGS. 10-14

In accordance with another embodiment, I provide a wire or core in the lumen of a hypodermic needle; such that when the needle is being used to cut a passageway through the patient's soft tissue, the wire will be partially withdrawn out of the way. However, when pressure is released, a spring will automatically replace the wire through the I.V. needle, thereby giving it protection.

Accordingly, as shown in FIG. 10, a wire 61 (solid or hollow, as a needle) is blunt ended at tip 63 and is fitted with a base 65. Wire 61 may be made of metal, plastic, wood, etc. Base 65 comprises a cylindrical unit 66 incorporating a compression spring 67 and a winged slide 69 with a plunger 71. The two wings or ears of slide 69 extend through longitudinal side slots 80 in unit 66. Wire 61 passes through a guide 73 in tapered spigot 75, and continues through the center of plunger 71 to an integral disc 77. This disc is sandwiched between end of spring 67, and the end of plunger 71, such that the wire can be moved back and forth through needle 61 by pulling back and then releasing pressure on winged slide 69.

I.V. cannula needle 81 is fitted with a tight fitting adapter 83, which, when mounted on wire 61, can be frictionally locked onto spigot 75. The tight-fit ensures that needle 81 will be withdrawn along with wire 61 and its adapter 65 when it is withdrawn from the patient.

Cannula 79 (FIG. 11) is a flexible barrel and is fitted onto needle 81. Its adapter 85 is loosely-fitted onto spigot 87 of adapter 83 (FIG. 10) This loose-fit insures that cannula 79 (FIG. 11) will remain in position in the patient when the I.V. needle is withdrawn.

FIG. 12 shows the position of wire end 63 in respect to cannula needle point 81′ and cannula end 79′ when the unit is in the "rest" position. Needle point 81′ is protected or shielded by protruding wire end 63 and thus cannot be used to stick anyone, accidentally or purposely.

FIG. 13 shows winged slide 69 has been pulled back as far as it will go in the direction of arrow "B". Plunger 71 has been pushed against disc 77, which in turn has pulled wire 63 back until its end tip 63 is inside the hollow cannula needle, and is no longer protecting it. Also plunger 71 has fully compressed spring 67. In this "ready" position, the I.V. needle is unprotected or unshielded can be inserted through the soft tissue while pressure is maintained on the winged slide.

Retracting the I.V. Needle

The user can choose to withdraw the needle part way before releasing hand pressure on the winged slide, or withdraw it fully, then release pressure. However, when pressure is released, the needle's point is will again be protected because spring 67 will force wire 63 back through needle 81 and out its end 81′ as shown in FIG. 12.

Summary, Ramifications and Scope

Thus it will be seen that I have provided two versions of a self-protecting I.V. cannula.

The first relies on the automatic shielding of a potentially dangerous hypodermic needle by the use of a built-in shield which effectively covers the needle as soon as pressure, which is used to inject the needle, is relaxed.

The other protects the needle from within by having a wire protruding through the needle itself. When pressure is applied to a winged cannula to force it to penetrate soft tissue, the wire is pulled back away from the needle's point, thus allowing it to cut a passageway. Hence the cannula is positioned in place and can be taped down before the needle and barrel is withdrawn. Alternatively, the needle and barrel can be withdrawn at the same time as pressure on the winged cannula is released. The needle will automatically be protected by the now protruding wire.

In both versions, the needle's sharp point is always fully and automatically protected, both before and after the insertion of the cannula assembly.

While the above description contains many specificities, the reader should not construe these as limitations on the scope of the invention but merely as exemplifications of preferred embodiments thereof. Those skilled in the art will envision that many other variations are within its scope. For example, skilled artsians will readily be able to change the dimensions, materials, shapes, and thicknesses of the various parts.

Accordingly, the reader is requested to determine the scope of the invention by the appended claims and their legal equivalents, and not by the examples which have been given.

I claim:
1. A cannula assembly, comprising:
an elongated needle having a sharpened tip, said needle having an axial lumen,
a cannula sleeve comprising an elongated member having a lumen sized to fit over said cannula needle so that said needle can be inserted coaxially within the lumen of said elongated member, and
shielding means having a shield position for normally shielding said tip of said needle so as to prevent a person from being intentionally or accidentally stuck with said tip, and for providing a manually operable member for allowing a user to manually move said member to an unshield position so as to unshield said tip when said needle and said cannula are to be inserted into a patient's body, said shielding means including urging means for urging said member to a shield position when said member is not manually held in its unshield position so that said tip of said needle will be shielded unless said member is manually moved to and held in its unshield position, said shielding means comprising a wire having a blunt end positioned in said lumen, one end of said wire normally protruding from said tip of said needle, the other end of said wire being attached to said member.

2. The cannnula assembly of claim 1 wherein said member comprises a pair of wings and further including a base adapter having a pair of slots through which said wings protrude.

3. The cannula assembly of claim 1 wherein said urging means comprises a coil spring arranged to urge said wire so that said one end thereof normally protrudes from said tip of said needle, and wherein said wire is made of metal.

4. A cannula assembly, comprising:
an elongated needle having a sharpened tip,
a cannula comprising an elongated tubular member having a lumen sized to fit over said elongated needle, said needle being inserted coaxially within said lumen of said cannula such that said sharpened tip of said needle projects from an end of said cannula,
shielding means which is manually moveable from a shield position to an unshield position,
said shielding means normally being in said shield position,
said shielding means, when in said shield position, extending beyond and thereby shielding said tip of said needle so as to prevent a person from being intentionally or accidentally stuck with said tip,
said shielding means being operably engaged with said cannula such that when said cannula is moved in a rearward direction away from said sharpened tip of said needle, said cannula will move said shielding means from said shield position to said unshield position,
a manually operable member attached to said cannula for allowing a user manually to move said manually operable member, and hence said cannula, in said rearward direction and thereby move said shielding means from said shield position to said unshield position,
said shielding means, when in said unshield position, uncovering and unshielding said tip of said needle such that said sharpened tip of said needle will be exposed so that said needle and said cannula can be inserted through a patient's skin, and urging means which
  (a) when said shielding means is in said shield position, continuously retains said shielding means in said shield position so as to resist movement of said shielding means away from said shield position, and
  (b) when said manually operable member and said cannula are manually moved in said rearward direction so that said shielding means is in said unshield position, urges said shielding means back to said shield position, such that said tip of said needle will always be shielded, unless said manually operable member is manually moved in said rearward direction so that said shielding means is in said unshield position.

5. The cannula assembly of claim 4 wherein said shielding means is a barrel comprising an elongated cylinder having a lumen sized to fit over said needle and within said cannula, said barrel being axially moveable along said needle and said cannula, and wherein said urging means normally urges said barrel to a position where one end of said barrel overlaps said tip of said needle so as to shield said tip of said needle.

6. The cannula assembly of claim 5 wherein said urging means is a spring.

7. The cannula assembly of claim 6 wherein said spring is attached to a base end of said barrel which is opposite said one end of said barrel, said needle having a base end opposite said tip of said needle, and further including a base adapter attached to said base end of said needle, said base adapter having a tubular extension for guiding said spring and said base of said barrel, said spring and said base end of said barrel being inserted into said cannula.

8. The cannula assembly of claim 4 wherein said manually operable member comprises a pair of wings extending from a base end of said cannula.

9. The cannula of claim 8 wherein said urging means comprises a spring.

10. The cannula assembly of claim 9 wherein said needle has a base end opposite said tip of said needle, and further including a base adapter attached to said base end of said needle, said base adapter having a tubular extension for guiding said spring.

11. The cannula assembly of claim 4 wherein said urging means is a coil spring.

12. The cannula assembly of claim 4 wherein said needle has an axial lumen and wherein said shielding means comprises a wire having a blunt end positioned in said lumen, one end of said wire normally protruding from said tip of said needle.

13. A cannula assembly, comprising:
an elongated needle having a sharpened tip,
a cannula comprising an elongated tubular member having a lumen sized to fit over said elongated needle, said needle being inserted coaxially within said lumen of said cannula such that said sharpened tip of said needle projects from an end of said cannula,
shielding means comprising an elongated barrel having a lumen sized to fit within said cannula and over said elongated needle, said needle and said shielding means being inserted coaxially within the lumen of said cannula, said barrel being manually moveable from a shield position to an unshield position,
said barrel normally being in said shield position, said barrel, when in said shield position, covering and thereby shielding said tip of said needle so as to prevent a person from being intentionally or accidentally stuck with said tip of said needle,
said barrel being operably engaged with said cannula such that when said cannula is moved in a rearward direction away from said sharpened tip of said needle, said cannula will move said barrel from said shield position to said unshield position,
a manually operable member attached to said cannula for allowing a user manually to move said cannula in said rearward direction, and hence move said barrel, from said shield position to said unshield position,
said barrel, when in said unshield position, uncovering and unshielding said tip of said needle such that said sharpened tip of said needle will be exposed so that said needle and said cannula can be inserted through a patient's skin, and
urging means which
  (a) when said barrel is in said shield position, continuously retains said barrel in said shield position so as to resist movement of said barrel away from said shield position, and
  (b) when said manually operable member is moved in said rearward direction so that said barrel is in said unshield position, urges said barrel back to said shield position, such that said tip of said needle will always be shielded, unless said manually operable member is manually moved in said rearward direction.

14. The cannula assembly of claim 13 wherein said urging means is a coil spring.

15. The cannula assembly of claim 14 wherein said barrel comprises a guideway which surrounds said spring.

16. The cannula assembly of claim 14 wherein said spring is attached to a base end of said barrel which is opposite said one end of said barrel, said needle having a base end opposite said tip of said needle, and further including a base adapter attached to said base end of said needle, said base adapter having a tubular extension for guiding said spring and said base of said barrel, said spring and said base end of said barrel being inserted into said cannula.

* * * * *